(12) United States Patent
Lanter et al.

(10) Patent No.: US 7,531,565 B2
(45) Date of Patent: May 12, 2009

(54) IMIDAZOLIDIN-2-ONE DERIVATIVES AS SELECTIVE ANDROGEN RECEPTOR MODULATORS (SARMS)

(75) Inventors: James C. Lanter, Raritan, NJ (US); Zhihua Sui, Raritan, NJ (US)

(73) Assignee: Janssen Pharmaceutica, N.V., Beerse (BE)

( * ) Notice: Subject to any disclaimer, the term of this patent is extended or adjusted under 35 U.S.C. 154(b) by 536 days.

(21) Appl. No.: 11/223,187

(22) Filed: Sep. 9, 2005

(65) Prior Publication Data

US 2006/0063819 A1    Mar. 23, 2006

Related U.S. Application Data

(60) Provisional application No. 60/609,157, filed on Sep. 10, 2004.

(51) Int. Cl.
    *A61K 31/4166*    (2006.01)
    *C07D 233/30*    (2006.01)

(52) U.S. Cl. .................... 514/386; 548/316.4

(58) Field of Classification Search ............ 548/316.4; 514/386
See application file for complete search history.

(56) References Cited

U.S. PATENT DOCUMENTS

| 4,097,578 A | 6/1978 | Perronnet et al. |
| 5,750,553 A | 5/1998 | Claussner et al. |
| 2005/0203078 A1 | 9/2005 | Priepke et al. |

FOREIGN PATENT DOCUMENTS

| DE | 2649925 A1 | 5/1977 |
| FR | 2715402 A1 | 7/1995 |
| FR | 2724169 A1 | 3/1996 |
| WO | WO 2005/082895 A1 | 9/2005 |

OTHER PUBLICATIONS

Ferm, Robert J. et al. "Synthesis of 2-imidazolines and 2-imidazolidones," Dept. of Chem., University of New Mexico, 1951. pp. 181-183.*

Kim, Taek Hyeon et al. article in J. Organic Chemistry, vol. 64(8), pp. 2941-2943, 1999.*
CAPLUS abstract of Schoellkopf, Ulrich et al. Accession No. 1980:495190.*
Basaria, S. et al.: Anabolic-Androgenic Steroid Therapy in the Treatment of Chronic Diseases, The J. of Clin. Endocrinology & Metabolism 2001 86(11), pp. 5108-5117.
Newling, D.W.W.: Anti-androgens in the treatment of prostate cancer, British J. of Urology (1996), 77, pp. 776-784.
Shahidi, N.T., MD.: A Review of the Chemistry, Biological Action, and Clinical Applications of Anabolic-Androgenic Steroids; Clinical Therapeutics, (2001) vol. 23, No. 9, pp. 1355-1391.
PCT Intl. Search Report, PCT/US2005/032381, Apr. 12, 2006.
Goubet, Francois et al. "Conversion of a Thiohydantoin to the Corresponding Hydantoin via a Ring-Opening/Ring Closure Mechanism". Tetrahedron Letters, 37(43), pp. 7727-7730, 1996. XP004030953.
Kim, Taek Hyeon et al. "Regiocontrolled Cyclization Reaction of N-(2-Hydroxyethyl)ureas by Transfer of Activation: One-Pot Synthesis of 2-Imidazolidinones". Journal of Organic Chemistry, 64(8), pp. 2941-2943, 1999. XP002374766.
Schollkopf, U. et al. "Syntheses with α-Metalated Isocyanides, XLV[1].—Reactions of α-Metalated Isocyanides with Some 1,3-Dipoles." Liebigs Ann. Chem. 1980 (4) pp. 600-610.

* cited by examiner

*Primary Examiner*—Rei-Tsang Shiao
*Assistant Examiner*—Janet L Coppins

(57) ABSTRACT

The present invention is directed to novel imidazolidin-2-one derivatives having a structure according to Formula I

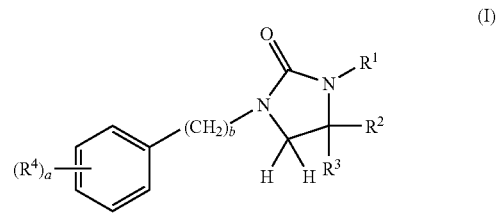

wherein a, b, $R^1$, $R^2$, $R^3$, and $R^4$ are as defined above, pharmaceutical compositions containing them and their use in the treatment of disorders and conditions modulated by the androgen receptor.

7 Claims, No Drawings

IMIDAZOLIDIN-2-ONE DERIVATIVES AS SELECTIVE ANDROGEN RECEPTOR MODULATORS (SARMS)

RELATED APPLICATION

This application claims the benefit of U.S. Provisional Application No. 60/609,157, filed Sep. 10, 2004, which is incorporated herein by reference in its entirety.

FIELD OF THE INVENTION

The present invention is directed to novel imidazolidin-2-one derivatives, pharmaceutical compositions containing them and their use in the treatment of disorders and conditions modulated by the androgen receptor. More particularly, the compounds of the present invention are useful in the treatment of prostate carcinoma, benign prostatic hyperplasia (BPH), hirsitutism, alopecia, anorexia nervosa, breast cancer, acne, AIDS, cachexia, as a male contraceptive, and/or as a male performance enhancer.

BACKGROUND OF THE INVENTION

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, agonists of the androgen receptor could be employed in the treatment of prostate cancer, benign prostatic hyperplasia, hirsutism in women, alopecia, anorexia nervosa, breast cancer and acne. Antagonists of the androgen receptor could be employed in male contraception, male performance enhancement, as well as in the treatment of cancer, AIDS, cachexia, and other disorders.

Nonetheless, there exists a need for small molecule, non-steroidal antagonists of the androgen receptor. We now describe a novel series of indole derivatives as androgen receptor modulators.

SUMMARY OF THE INVENTION

The present invention is directed to a compound of formula (I)

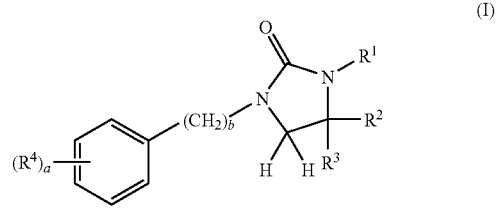

wherein:
  $R^1$ is selected from the group consisting of hydrogen and lower alkyl;
  $R^2$ and $R^3$ are independently selected from the group consisting of lower alkyl, halogen substituted lower alkyl, —CH(OH)-(lower alkyl), —C(O)-(lower alkyl), —C(O)-(lower alkoxy), —C(O)—N($R^4$)$_2$, —C(O)—N($R^B$)$_2$ provided that one of $R^2$ or $R^3$ is either lower alkyl or halogen substituted lower alkyl;
  wherein each $R^A$ is independently selected from hydrogen or lower alkyl;
  wherein each $R^B$ is independently selected from hydrogen, lower alkyl and aryl provided that if present, only one $R^B$ is aryl;
  wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;
  $R^4$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—N($R^A$)$_2$, —S(O)$_{0-2}$-(lower alkyl), —SO$_2$—N($R^A$)$_2$, —N($R^A$)—C(O)-(lower alkyl), —N($R^A$)—C(O)-(halogen substituted lower alkyl) and aryl;

wherein each $R^A$ is independently selected from hydrogen or lower alkyl; wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

a is an integer from 0 to 4;

b is an integer from 0 to 1;

or a pharmaceutically acceptable salt thereof.

In one aspect, the invention relates to a pharmaceutical composition comprising a pharmaceutically acceptable carrier and any of the compounds described herein. In another aspect, the invention relates to a pharmaceutical composition made by mixing any of the compounds described herein and a pharmaceutically acceptable carrier. In yet another aspect the invention is a process for making a pharmaceutical composition comprising mixing any of the compounds described herein and a pharmaceutically acceptable carrier.

The invention also provides methods of treating disorders and conditions modulated by the androgen receptor in a subject in need thereof comprising administering to the subject a therapeutically effective amount of any of the compounds or pharmaceutical compositions described herein.

In a preferred embodiment invention provides a method for treating an androgen receptor modulated disorder selected from the group consisting of prostate carcinoma, benign prostatic hyperplasia, hirsutism, or for male contraception, in a subject in need thereof comprising administering to the subject an effective amount of any of the compounds or pharmaceutical compositions described herein.

Another example of the invention is the use of any of the compounds described herein in the preparation of a medicament for treating: (a) prostate carcinoma, (b) benign prostatic hyperplasia, (c) hirsutism, (d) alopecia, (e) anorexia nervosa, (f) breast cancer, (g) acne, (h) AIDS, (i) cachexia, for (j) male contraception, or for (k) male performance enhancement, in a subject in need thereof.

DETAILED DESCRIPTION OF THE INVENTION

The present invention is directed to compounds of formula (I),

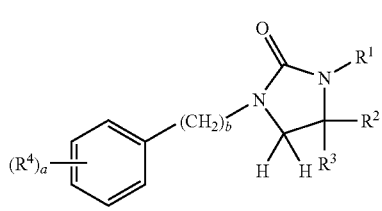

wherein a, b, $R^1$, $R^2$, $R^3$, and $R^4$ are as defined above. Where the compounds according to this invention have at least one chiral center, they may accordingly exist as enantiomers. The compounds of the present invention are modulators of the androgen receptor and are useful for the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

Representative compounds of the present invention are as listed in Table 1.

TABLE 1

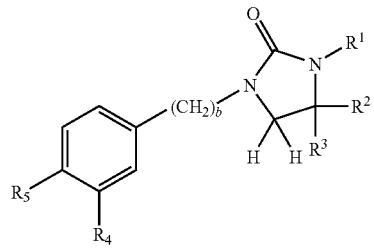

| COMPOUND | R1 | R2 | R3 | R4 | R5 | b |
|---|---|---|---|---|---|---|
| 4a | H | Me | $CO_2Me$ | H | F | 0 |
| 5a | H | Me | $CO_2H$ | H | F | 0 |
| 4c | H | Me | $CO_2Me$ | H | OMe | 0 |
| 5c | H | Me | $CO_2H$ | H | OMe | 0 |
| 6c | H | Me | NH(4-CN, 3-$CF_3$-phenyl) | H | OMe | 0 |
| 6a | H | Me | NH(4-CN, 3-$CF_3$-phenyl) | H | F | 0 |
| 4b | H | Me | $CO_2Me$ | H | H | 0 |
| 5b | H | Me | $CO_2H$ | H | H | 0 |
| 6b | H | Me | NHPh | H | H | 0 |
| 6d | H | Me | NH(4-CN, 3-$CF_3$-phenyl) | H | H | 0 |
| 6e | H | Me | NH(4-$NO_2$, 3-$CF_3$-phenyl) | H | H | 0 |
| 6j | H | Me | NH(6-$CF_3$-pyridin-3-yl) | H | H | 0 |
| 6f | H | Me | NH(4-Cl, 3-$CF_3$-phenyl) | H | F | 0 |
| 6g | H | Me | NH(3-$CF_3$-phenyl) | H | F | 0 |
| 6h | H | Me | NH(3,5-bis-$CF_3$-phenyl) | H | F | 0 |
| 4d | H | Me | $CO_2Me$ | $CF_3$ | Cl | 0 |
| 5d | H | Me | $CO_2H$ | $CF_3$ | Cl | 0 |
| 4e | H | Me | $CO_2Me$ | $CF_3$ | CN | 0 |
| 5e | H | Me | $CO_2H$ | $CF_3$ | CN | 0 |
| 4f | H | Me | $CO_2Me$ | $CF_3$ | OMe | 0 |
| 6i | H | Me | NH(4-CN, 3-$CF_3$-phenyl) | H | F | 1 |
| 4h | H | Me | $CO_2Me$ | H | OMe | 1 |

As used herein, unless otherwise noted, the term "halogen" shall mean chlorine, bromine, fluorine and iodine.

As used herein, unless otherwise noted, the term "alkyl", whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, the term "halogen substituted lower alkyl" shall mean a lower alkyl group as defined above wherein one or more of the hydrogen atoms is replaced with a halogen atom. Suitable examples include, but are not limited to, trifluoromethyl, 2,2,2-trifluoro-eth-1-yl, chloromethyl, fluoromethyl and the like. Similarly, the term "fluorinated lower alkyl" shall mean a lower alkyl group as defined above wherein one or more of the hydrogen atoms is replaced with a fluorine atom. Suitable examples include, but are not limited to, fluoromethyl, fluoroethyl, trifluoromethyl, 2,2,2-trifluoro-eth-1-yl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "cycloalkyl" shall mean any stable four to eight membered monocyclic, saturated ring system, for example cyclobutyl, cyclopentyl, cyclohexyl, cycloheptyl and cyclooctyl.

As used herein, unless otherwise noted, "aryl" shall refer to unsubstituted carbocylic aromatic groups such as phenyl, naphthyl, and the like.

As used herein, unless otherwise noted, "heteroaryl" shall denote any five or six membered, monocyclic aromatic ring structure containing at least one heteroatom selected from the group consisting of O, N and S, optionally containing one to three additional heteroatoms independently selected from the group consisting of O, N and S; or a nine or ten membered, bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the notation "*" shall denote the presence of a stereogenic center.

When a particular group is "substituted" (e.g., cycloalkyl, aryl, heteroaryl, etc), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)" substituent refers to a group of the formula

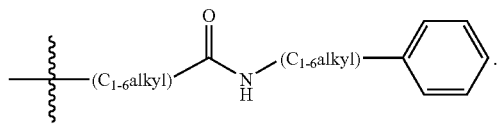

Abbreviations used in the specification, particularly the Schemes and Examples, are as follows:

| | |
|---|---|
| AR = | Androgen Receptor |
| BPH = | Benign Prostatic Hyperplasia |
| DCM = | Dichloromethane |
| DIPEA or DIEA or IPr$_2$NEt = | Diisopropylethylamine |
| DHT = | Dihydrotestosterone |
| DMEM/F12 = | Dulbecco's modified Eagle's medium/F12 |
| DMF = | N,N-Dimethylformamide |
| DMSO = | Dimethylsulfoxid |
| DTT = | Dithiothreitol |
| EDTA = | Ethylene diamine tetraacetic acid |
| MeOH = | Methanol |
| NMR = | Nuclear Magnetic Resonance |
| TE or TED Buffer = | Tris HCl + EDTA (Tetraacetic Acid Ethylene Diamine) |
| TEA or Et$_3$N = | Triethylamine |
| THF = | Tetrahydrofuran |
| Tris HCl = | Tris[hydroxymethyl]aminomethyl hydrochloride |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes, but is not limited to, alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1 below.

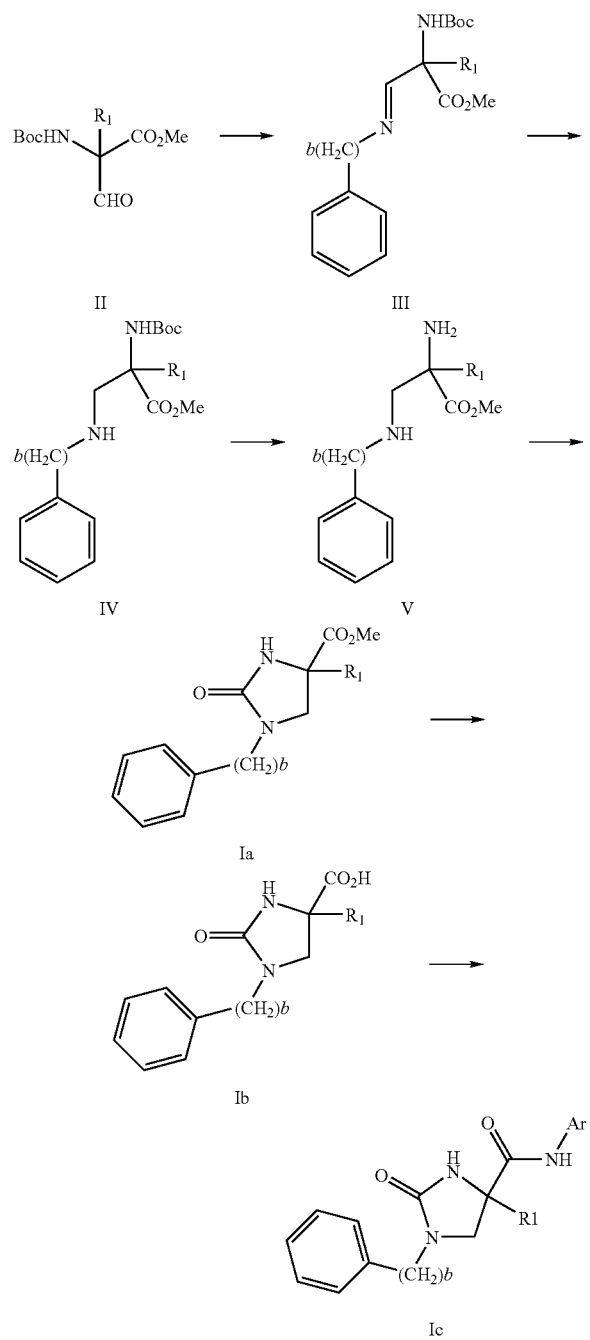

Accordingly, a suitably substituted compound of formula (II), a known compound or compound prepared by known methods, is reacted with a primary benzyl (b=1) or aryl (b=0) amine in an organic solvent or mixture thereof, such as benzene, toluene, xylene, and the like, optionally in the presence of a catalyst, such as toluene sulfonic acid, benzene sulfonic acid, sulfuric acid and the like, is heated under Dean-Stark conditions to yield the corresponding compound of formula (III). Alternatively, a mixture of the compound of formula (II) and the corresponding primary benzyl (b=1) or aryl (b=0) amine in an organic solvent such as THF, methanol, ethanol, and the like is reacted with a reducing agent such as sodium cyanoborohydride, sodium triacetoxyborohydride and the like, to yield the corresponding compound of formula (IV) directly.

The compound of formula (III) is reacted with a reducing agent such as hydrogen gas (in the presence of a palladium catalyst), sodium borohydrde, sodium cyanoborohydride and the like in an organic solvent such as methanol, ethanol, THF and the like, to yield the corresponding compound of formula (IV).

The compound of formula (IV) is de-protected according to known methods, for example, by reacting with an acid such as trifluoromethanesulfonic acid, HCl, trifluoroacetic acid, and the like, in an organic solvent or mixture thereof such as methanol/water, ethanol/water, THF, and the like, to yield the corresponding compound of formula (V).

The compound of formula (V) is reacted with a reagent such as carbonyl diimidazole, p-nitrophenylchloroformate, triphosgene, phosgene and the like in the presence of a base such as triethylamine, pyridine, and the like, in an organic solvent such as THF, dichloromethane and the like, to yield the corresponding compound of formula Ia. Alternatively, the compound of formula (Ia) is reacted with a base such as sodium hydroxide, potassium hydroxide and the like, in an organic solvent or mixture thereof such as methanol/water, ethanol/water, THF, and the like, to yield the corresponding compound of formula (Ib). Alternatively, the compound of formula (Ib) is reacted with oxalyl chloride in a solvent such as dichloromethane, dichloroethane and the like, optionally in the presence of a catalytic amount of DMF, to form the intermediate acid chloride which is reacted with an appropriately substituted primary amine to afford the corresponding compound of formula (Ic).

The following Examples are set forth to aid in the understanding of the invention, and are not intended and should not be construed to limit in any way the invention set forth in the claims which follow thereafter.

EXAMPLE 1

2-tert-Butoxycarbonylamino-3-(4-fluoro-phenylamino)-2-methyl-propionic acid methyl ester (1a)

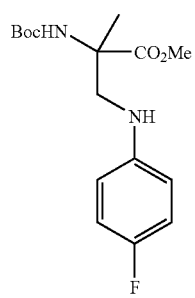

To a solution of 2-tert-butoxycarbonylamino-2-methyl-3-oxo-propionic acid methyl ester (2.35 g, 6.71 mmol) in methanol (25 mL) was added 4-fluoroaniline (0.53 mL, 5.59 mmol) and acetic acid (0.16 mL, 2.80 mmol). A solution of sodium cyanoborohydride (188 mg, 2.99 mmol) in methanol (25 mL) was added dropwise and the reaction mixture stirred for 3 hours at room temperature post addition. The solvent was removed in vacuo and the residue dissolved in DCM (50 mL). The organic solution was treated with aqueous sodium carbonate solution (20 mL, 1N), stirred for 20 min, and the aqueous layer removed. Concentration of the organic layer followed by purification of the residue using flash chromatography ($SiO_2$, DCM) afforded the title compound as a yellow oil (970 mg, 53%).

TABLE A

MS(m/Z) = 325 (M − H)
Analogs produced using the procedure described in Example 1.

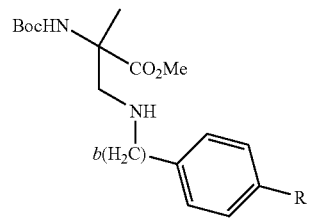

| COMPOUND | R | b | Yield | MS |
|---|---|---|---|---|
| 1b | H | 0 | 78% | 307 (M − H) |
| 1c | OMe | 0 | 87% | 337 (M − H) |
| 1d | F | 1 | 35% | 341 (MH+) |

EXAMPLE 2

2-tert-Butoxycarbonylamino-3-(4-methoxy-benzylamino)-2-methyl-propionic acid methyl ester (2a)

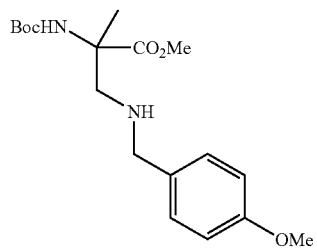

To a solution of 2-tert-butoxycarbonylamino-2-methyl-3-oxo-propionic acid methyl ester (1.40 g, 6.06 mmol) in toluene (70 mL) was added 4-methoxybenzylamine (0.80 mL, 6.12 mmol) and p-toluenesulfonic acid (ca. 10 mg). The flask was fitted with a Dean-Stark trap and a reflux condenser and heated to reflux under nitrogen for 2 hours. The solvent was removed in vacuo to afford the imine as a yellow oil that was of suitable purity for further use.

This residue was dissolved in methanol (30 mL). A solution of sodium borohydride (310 mg, 8.17 mmol) in methanol (15 mL) was added dropwise and the reaction mixture stirred for 3 hours at room temperature post addition. The solvent was removed in vacuo and the residue dissolved in DCM (50 mL). The organic solution was treated with aqueous sodium carbonate solution (20 mL, 1N), stirred for 20 min, and the aqueous layer removed. Concentration of the organic layer followed by purification of the residue using flash chromatography (SiO$_2$, DCM) afforded the title compound as a yellow oil (1.85 g, 99%).

TABLE B

MS(m/Z) = 353 (MH+)
Analogs produced using the procedure described in Example 2.

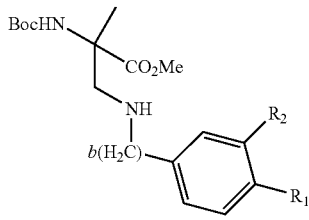

| Compound | R$_1$ | R$_2$ | b | Yield | MS |
|---|---|---|---|---|---|
| 2b | Cl | CF$_3$ | 0 | 25% | 410 (M − H) |
| 2c | OMe | CF$_3$ | 0 | 82% | 405 (M − H) |
| 2d | CN | CF$_3$ | 0 | 45% | 400 (M − H) |

EXAMPLE 3

2-Amino-3-(4-fluoro-phenylamino)-2-methyl-propionic acid methyl ester (3a)

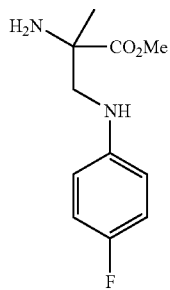

To a solution of 2-tert-butoxycarbonylamino-3-(4-fluoro-phenylamino)-2-methyl-propionic acid methyl ester (954 mg, 2.92 mmol) in methanol (10 mL) was added HCl (3 mL, 12 N). The mixture was heated to 55° C. until the MS indicated no starting material remained. After cooling to ambient temperature, the solution was treated with aqueous NaOH (40 mL, 1N) and extracted several times with DCM. The combined extracts were concentrated and purified by flash chromatography (SiO$_2$, 5% MeOH/DCM) to yield the title compound as a yellow oil (305 mg, 46%).

TABLE C

MS (m/Z) = 227 (MH+)
Analogs produced using the procedure described in Example 3.

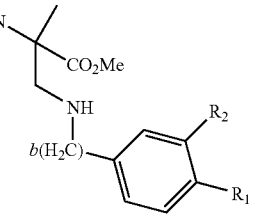

| Compound | R$_1$ | R$_2$ | b | Yield | MS (MH+) |
|---|---|---|---|---|---|
| 3b | H | H | 0 | 78% | 209 |
| 3c | OMe | H | 0 | 87% | 239 |
| 3d | Cl | CF$_3$ | 0 | 99% | 312 |
| 3e | CN | CF$_3$ | 0 | 64% | 302 |
| 3f | OMe | CF$_3$ | 0 | 38% | 307 |
| 3g | F | H | 1 | 88% | 241 |
| 3h | OMe | H | 1 | 99% | 253 |

EXAMPLE 4

1-(4-Fluoro-phenyl)-4-methyl-2-oxo-imidazolidine-4-carboxylic acid methyl ester (4a)

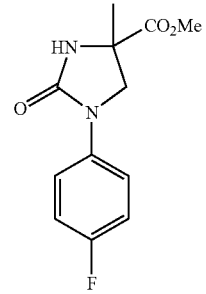

A solution of 2-amino-3-(4-fluoro-phenylamino)-2-methyl-propionic acid methyl ester (282 mg, 1.25 mmol) in THF (10 mL) was treated with triethylamine (2.00 mL, 14.3 mmol) and cooled to 0° C. under argon. A solution of triphosgene (211 mg, 0.71 mmol) was added to the reaction dropwise and the mixture allowed to reach room temperature. After 1 hour, the mixture was diluted with DCM, washed with 1N HCl and the organic layers concentrated in vacuo. The resulting residue was purified by flash chromatography to afford the product (260 mg, 82%).

TABLE D

MS(m/Z) = 251 (M − H)
Other compounds produced using the procedure described in Example 4.

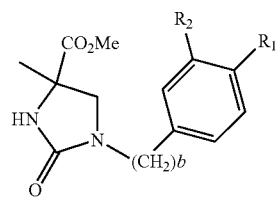

| Compound | R$_1$ | R$_2$ | b | Yield | MS (M − H) |
|---|---|---|---|---|---|
| 4b | H | H | 0 | 50% | 233 |
| 4c | OMe | H | 0 | 66% | 263 |

TABLE D-continued

MS(m/Z) = 251 (M − H)
Other compounds produced using the procedure described in Example 4.

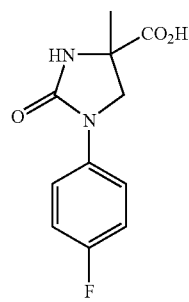

| Compound | $R_1$ | $R_2$ | b | Yield | MS (M − H) |
|---|---|---|---|---|---|
| 4d | Cl | $CF_3$ | 0 | 58% | 336 |
| 4e | CN | $CF_3$ | 0 | 63% | 326 |
| 4f | OMe | $CF_3$ | 0 | 80% | 331 |
| 4g | F | H | 1 | 33% | 265 |
| 4h | OMe | H | 1 | 57% | 277 |

EXAMPLE 5

1-(4-Fluoro-phenyl)-4-methyl-2-oxo-imidazolidine-4-carboxylic acid (5a)

A solution of 1-(4-fluoro-phenyl)-4-methyl-2-oxo-imidazolidine-4-carboxylic acid methyl ester (247 mg, 0.98 mmol) in methanol (15 mL) was treated with aqueous NaOH (1.50 mL, 6.38 mmol). After stirring 1 hour at room temperature, the mixture was treated with 1N HCl to pH 1 and the resulting white precipitate collected by filtration (135 mg, 58%).

TABLE E

MS(m/Z) = 237 (M − H)
Other compounds produced using the procedure described in Example 5.

| Compound | $R_1$ | $R_2$ | b | Yield | MS (M − H) |
|---|---|---|---|---|---|
| 5b | H | H | 0 | 89% | 219 |
| 5c | OMe | H | 0 | 77% | 249 |
| 5d | Cl | $CF_3$ | 0 | 94% | 321 |
| 5e | CN | $CF_3$ | 0 | 35% | 312 |
| 5f | OMe | $CF_3$ | 0 | 52% | 317 |
| 5g | F | H | 1 | 65 | 251 |

EXAMPLE 6

1-(4-Fluoro-phenyl)-4-methyl-2-oxo-imidazolidine-4-carboxylic acid (4-cyano-3-trifluoromethyl-phenyl)-amide (6a)

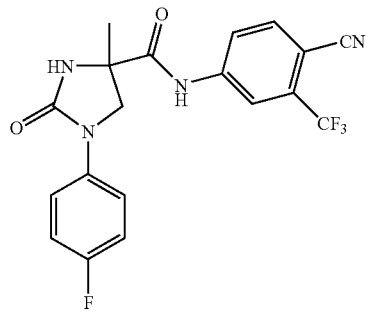

A solution of 1-(4-fluoro-phenyl)-4-methyl-2-oxo-imidazolidine-4-carboxylic acid (120 mg, 0.50 mmol) in DCM (15 mL) was treated oxalyl chloride (0.09 mL, 1.03 mmol) and one drop of dry DMF. After stirring 1 hour at room temperature, the solvent was removed in vacuo. To this residue, a solution of 4-amino-2-(trifluoromethyl)benzonitrile (277 mg, 1.49 mmol) and triethylamine (0.28 mL, 2.01 mmol) in dry DCM (10 mL) was added. After stirring overnight at room temperature, the mixture was concentrated in vacuo and the residue purified by flash chromatography to afford the title compound as a tan solid (110 mg, 54%).

TABLE F

MS(m/Z) = 405 (M − H)
Other compounds produced using the procedure described in Example 6.

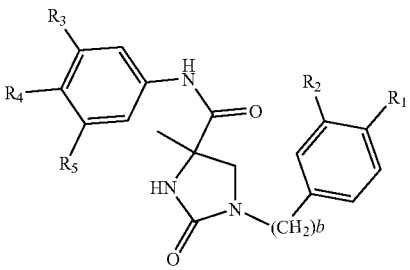

| Compound | R₁ | R₂ | R₃ | R₄ | R₅ | b | Yield | MS |
|---|---|---|---|---|---|---|---|---|
| 6b | H | H | H | H | H | 0 | 35% | 296 (MH+) |
| 6c | OMe | H | CF₃ | CN | H | 0 | 28% | 417 (M − H) |
| 6d | H | H | CF₃ | CN | H | 0 | 26% | 389 (MH+) |
| 6e | H | H | CF₃ | NO₂ | H | 0 | 23% | 409 (MH+) |
| 6f | F | H | CF₃ | Cl | H | 0 | 30% | 415 (M − H) |
| 6g | F | H | CF₃ | H | H | 0 | 26% | 382 (MH+) |
| 6h | F | H | CF₃ | H | CF₃ | 0 | 20% | 450 (MH+) |
| 6i | F | H | CF₃ | CN | H | 1 | 53% | 419 (M − H) |
| 6j | H | H | (N) | CF3 | H | 0 | 70% | 365 (MH+) |

EXAMPLE 7

Androgen Receptor Binding Using Rat Ventral Prostate Cytosol

Rat Prostate Cytosol Preparation:

Male Sprague Dawley or Wistar rats (Charles River, 200-300 g) were used for each preparation. The day before preparing the cytosol, the rats were castrated using standard surgical procedures.

The rats were euthanized by carbon dioxide asphyxiation. The rat prostates were quickly removed and placed on ice in pre-chilled, pre-weighed 50 mL plastic tubes. No more than five prostates were placed into one tube. The tubes were then weighed and the prostate tissue wet weights calculated. To the chilled prostate tissue was then added 1 mL/mg tissue of chilled homogenization buffer. The homogenization buffer was freshly prepared by mixing 10 mM Tris.HCl, pH 7.4, 1 mM sodium molybdate, 1.5 mM EDTA, 1 mM dithiothreitol, 10% (v/v) glycerol and 1% protease inhibitor cocktail (Sigma P 8340).

The prostate tissue was homogenized in a cold room using a pre-chilled Polytron PT3000 homogenizer (Brinkmann). Homogenization was performed at a speed setting of 20, three times for 10 sec bursts. The tubes containing the prostate tissue was kept on ice while homogenizing. The homogenate was allowed to rest on ice for 20 sec between bursts.

The homogenate was then placed into pre-chilled 3 mL polycarbonate ultracentrifuge tubes and centrifuged in the TLA-100 rotor of a TL-100 ultracentrifuge for 12 min at 100,000 rpm at 4° C. The resulting supernatant was stored in 1 mL aliquots at −80° C. until needed.

Binding to the androgen receptor was determined according to the protocol described in Example 86 using the above prepared rat cytosol. % Inhibition was determined by testing dilutions of the test compound (usually duplicates of 10 μM) in the binding assay. Counts per well were measured and percents of inhibition determined. Androgen receptor binding $IC_{50}$s were determined by testing serial dilutions of the test compound (usually duplicate ten half-log dilutions starting at 10 μM) in the binding assay. Counts per well were measured and $IC_{50}$s determined by linear regression.

Representative compounds of the present invention were tested for binding to the androgen receptor according to the procedure described above with results as listed in Table B. For compounds tested more than once, each result is listed separately in the Table 2 below.

TABLE 2

ANDROGEN RECEPTOR BINDING (RAT CYTOSOL)

| COMPOUND | % Inhibition @ 3 μM |
|---|---|
| 4a | −57 |
| 5a | 33 |
| 4c | −36 |
| 5c | −21 |
| 6c | 29 |
| 6a | 63 |
| 4b | −71 |
| 5b | −110 |
| 6b | −68 |
| 6d | 1 |
| 6e | −71 |
| 6j | −75 |
| 6f | 66 |
| 6g | 23 |
| 6h | −17 |
| 4d | 24 |
| 5d | 28 |
| 4e | −68 |
| 5e | −67 |
| 6i | 4 |

EXAMPLE 8

COS-7 Whole-Cell Androgen Receptor Binding Assay, Adenovirus Transduction

Day One:

COS-7 cells were plated in 96-well plates at 20,000 cells per well, in a solution of DMEM/F12 (GIBCO) containing 10% (v/v) charcoal-treated fetal bovine serum (Hyclone) and lacking phenol red. The cells were then incubated overnight at 37° C. in 5% (v/v) humidified $CO_2$.

Day Two:

Test compound solutions were prepared by diluting the test compound in 100% (v/v) DMSO, if necessary. Each dilution yielded a solution which was 625× the final desired test concentration.

Next, 1 mL of DMEM/F12 lacking phenol red was pipetted into each of the wells of a 2-mL 96-well assay block. Then 4 μL of the 625× test compound dilutions were pipetted into each well of the assay block. The wells were carefully mixed by pipette.

In a 15 mL or 50 mL sterile centrifuge tube, a 2.5 nM dilution of tritiated methyl-trienolone in DMEM/F12 lacking phenol red ([³H]R1881; Perkin-Elmer) was prepared.

In a 15 mL or 50 mL sterile centrifuge tube, a dilution in DMEM/F12 of the adenovirus AdEasy+rAR at a moi of 1:50 per well was prepared.

The medium was removed from the 96-well plates by inversion and the plates dried very briefly, inverted, on a sterile towel. As soon as possible after medium removal, 40 μL of the diluted test compound was added to each well, in duplicate. To each well was then added 40 μL of the 2.5 nM

[³H]R1881 and 20 μL of the diluted adenovirus. The plates were then incubated for 48 hours at 37° C. in 5% (v/v) humidified $CO_2$.

Day Four:

The medium was removed from the above incubated plates by inversion and dried. Each well was then washed with 0.35 mL of 1×PBS. The PBS was then removed from the plates by inversion and the plates dried.

To each well was then added 50 μL of 0.5% (v/v) Triton X-100 (Sigma) in 1×PBS and the plates placed on a rotary shaker for 5 min. The contents of each well were then transferred to an OptiPlate-96 (Packard) scintillation plate. To each well was then added 0.2 mL of Microscint-20 (Packard) and the wells counted on a TopCount (Packard).

Percent inhibition was determined by testing dilutions of the test compound (usually duplicates of 10 μM) in the binding assay. Counts per well were measured and percents of inhibition determined. Androgen receptor binding $IC_{50}$s were determined by testing serial dilutions of the test compound (usually duplicate ten half-log dilutions starting at 10 μM) in the binding assay. Counts per well were measured and $IC_{50}$s determined by linear regression.

Representative compounds of the present invention were tested for binding to the androgen receptor according to the procedure described above with results as listed in Table C. Unless otherwise noted, COS binding % inhibition was determined using a concentration of 3000 nM. For compounds tested more than once, each result is listed separately in Table 3 below.

TABLE 3

COS Binding

| COMPOUND | % Inhibition @ 3 μM |
|---|---|
| 4a | −20 |
| 5a | −14 |
| 4c | −8 |
| 5c | −11 |
| 6c | 24 |
| 6a | 43 |
| 4b | 16 |
| 5b | 15 |
| 6b | 22 |
| 6d | 40 |
| 6e | 37 |
| 6j | 18 |
| 6f | 35 |
| 6g | −40 |
| 6h | 76 |
| 4d | −30 |
| 5d | −26 |
| 4e | 27 |
| 6i | 28 |

EXAMPLE 9

L929 Androgen Receptor Functional Assay, Adenovirus Transduction

Day One:

L929 cells were plated in 96-well plates at 20,000 cells per well, in DMEM/F12 (GIBCO) containing 10% (v/v) charcoal-treated fetal bovine serum (Hyclone) and lacking phenol red. The plates were then incubated overnight at 37° C. in 5% (v/v) humidified $CO_2$.

Day Two:

Test compound dilutions were prepared in 100% (v/v) DMSO, if necessary. Each dilution was made to 1250× the final desired assay concentration. First, 2 mL of DMEM/F12 lacking phenol red was pipetted into the wells of a 2-mL 96-well assay block. Next, 4 μL of the 1250× test compound dilutions were pipetted into each well of the assay block. The mixtures within the well were then carefully mixed by pipette.

In a 15 mL or 50 mL sterile centrifuge tube, a 2.5 nM (2.5×) dilution of R1881 (methyl-trienolone) in DMEM/F12 lacking phenol red was prepared. In a second 15 mL or 50 mL centrifuge tube a solution containing an equal volume of DMEM to the first and an equal volume of 100% (v/v) DMSO to the volume of R1881 used in the first tube was prepared.

In a 15 mL or 50 mL sterile centrifuge tube, a dilution in DMEM/F12 of the adenovirus AdEasy+rAR at an moi of 1:500 per well was prepared. The medium was removed from the 96-well plates by inversion and dried, inverted, very briefly. As soon as possible after medium removal, 40 μL of the diluted unlabeled test compound was added to each well, in duplicate. To each well designated for antagonist testing was added 40 μL of the 2.5 nM R1881 dilution to the wells for antagonist testing. To each well designated for agonist testing was added 40 μL of the DMSO dilution. Then 20 μL of the diluted adenovirus were added to all wells. The plates were incubated for 48 hours at 37° C. in 5% (v/v) humidified $CO_2$.

Day Four:

To each well was added 100 μL of Steady-Glo luciferase assay substrate (Promega) and the plates were placed on a rotary shaker for 1 min. The plates were then incubated at room temperature in the dark for one hour. The contents of each well were then transferred to a white microtiter plate (Packard) and read on a Luminoskan Ascent (Thermo Lab Systems).

L929 AR percent activity was determined by testing dilutions of the test compound using a concentration of 3000 nM unless otherwise noted. L929 percent inhibition was determined by testing dilutions of the test compound using a concentration of 3000 nM. $EC_{50}$s and $IC_{50}$s were determined by testing serial dilutions of the test compound (usually duplicate ten half-log dilutions starting at 10 μM). Luciferase activity per well were measured and $EC_{50}$s and $IC_{50}$s determined by linear regression.

Representative compounds of the present invention were tested for functional activity at the androgen receptor according to the procedure described above with results as listed in Table 4.

TABLE 4

L929 Androgen Receptor Functional Assay

| COMPOUND | % Activation @ 3 μM | % Inhibition @ 3 μM |
|---|---|---|
| 4a | 0 | −20 |
| 4c | 2 | 5 |
| 5c | −5 | −14 |
| 6c | 0 | 11 |
| 6a | 9 | 37 |
| 4b | 0 | 34 |
| 5b | 0 | 32 |
| 6b | 0 | 54 |
| 6d | 0 | 59 |
| 6e | 2 | 96 |
| 6j | 0 | 29 |
| 5a | 1 | 15 |
| 6f | 3 | 85 |

TABLE 4-continued

L929 Androgen Receptor Functional Assay

| COMPOUND | % Activation @ 3 μM | % Inhibition @ 3 μM |
|---|---|---|
| 6g | 0 | −12 |
| 6h | 0 | 21 |
| 4d | 0 | 1 |
| 5d | 0 | −30 |
| 4e | 0 | −15 |
| 5e | 0 | 30 |
| 6i | 0 | 76 |

EXAMPLE 10

Ventral Prostate and Seminal Vesicle Weight In Vivo Assay

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle) and with testosterone propionate (given subcutaneously by injection at the nape of the neck at 2 mg/kg, in a volume of 0.1 mL in sesame oil). On the sixth day, the rats were euthanized by asphyxiation in carbon dioxide. Ventral prosatates and seminal vesicles were removed and their wet weights determined. Test compound activity was determined as the percent inhibition of testosterone-enhanced tissue weights, with a vehicle-treated control group set to zero percent and a testosterone alone-treated control group set to 100%.

A test compound was said to be "active" if the non weight adjusted prostate weight was $\leq 60$ mg or $\geq 84$ mg.

Compounds 6a, 4b, 6h, 4e and 5e were tested according to the procedure described above and determined to be "active".

Compounds 6e, 6j, 5a, 4a, 6g, 4d, 5d, 4c, 5c, 6c, 5b, 6b, 6d, and 6e were tested according to the procedure described above and determined to be "inactive". Note that while certain of these compounds may or may not have shown an effect on prostate and/or vesical weight, they are listed herein as "inactive" as they did not meet the specified criteria defined above.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound selected from the group consisiting of: 4-Methyl-2-oxo-1-phenyl-imidazolidine-4-carboxylic acid phenylamide; 4-Methyl-2-oxo-1-phenyl-imidazolidine-4-carboxylic acid (4-nitro-3-trifluoromethyl-phenyl)-amide; 4-Methyl-2-oxo-1-phenyl-imidazolidine-4-carboxylic acid (4-cyano-3-trifluoromethyl-phenyl)-amide; 1-(4-Fluoro-benzyl)-4-methyl-2-oxo-imidazolidine-4-carboxylic acid (4-cyano-3-trifluoromethyl-phenyl)-amide; and 1-(4-Fluoro-phenyl)-4-methyl-2-oxo-imidazolidine-4-carboxylic acid (4-chloro-3-trifluoromethyl-phenyl)-amide.

2. A compound of having the formula 1-(4-Fluoro-phenyl)-4-methyl-2-oxo-imidazolidine-4-carboxylic acid (4-cyano-3-trifluoromethyl-phenyl)-amide.

3. A compound of having the formula 1-(4-Fluoro-phenyl)-4-methyl-2-oxo-imidazolidine-4-carboxylic acid (3,5-bis-trifluoromethyl-phenyl)-amide.

4. A compound of having the formula 4-Methyl-2-oxo-1-phenyl-imidazolidine-4-carboxylic acid methyl ester.

5. A compound of having the formula 1-(4-Cyano-3-trifluoromethyl-phenyl)-4-methyl-2-oxo-imidazolidine-4-carboxylic acid methyl ester.

6. A compound of having the formula 1-(4-Cyano-3-trifluoromethyl-phenyl)-4-methyl-2-oxo-imidazolidine-4-carboxylic acid.

7. A pharmaceutical composition comprising a pharmaceutically acceptable carrier and a compound as in any of claims 1-6.

* * * * *